United States Patent [19]
Douglas-Hamilton et al.

[11] Patent Number: 5,093,866
[45] Date of Patent: Mar. 3, 1992

[54] FLUORESCENCE AND MOTILITY CHARACTERIZATION SYSTEM FOR CELLS, BACTERIA, AND PARTICLES IN FLUIDS

[75] Inventors: Diarmaid H. Douglas-Hamilton, Beverly; Paul R. Loomis, Groveland; Paul Boisseau; William P. Nett, both of Waltham, all of Mass.

[73] Assignees: Hamilton Equine Associates Limited; Laura Thorn Ltd., both of Danvers, Mass.

[21] Appl. No.: 478,205

[22] Filed: Feb. 9, 1990

[51] Int. Cl.[5] ............................................. G06K 9/00
[52] U.S. Cl. .............................................. 382/6; 382/1; 356/39; 364/413.1
[58] Field of Search ................... 382/6, 1; 358/107; 364/413.08, 413.1; 356/39, 441, 442

[56] References Cited
U.S. PATENT DOCUMENTS 3,824,402  7/1974  Mullaney et al. .................. 250/565
4,243,318  1/1981  Stöhr ................................. 356/39
4,284,412  8/1981  Hansen et al. ..................... 23/230 B
4,573,195  2/1986  de France ......................... 382/6
4,896,967  1/1990  Hamilton et al. ................. 356/442

OTHER PUBLICATIONS

Leif et al., "Development of Instrumentation and Fluorchromes for Automated Multiparameter Analysis of Cells", Clinical Chemistry, vol. 23, No. 8, 1977, pp. 1492-1498.
Ku era et al., "Computer-Controlled Double-Beam Scanning Microspectrophotometry for Rapid Microscopic Image Reconstructions", J. of Microscopy, vol. 116, 7/79, pp. 173-184.

Primary Examiner—Leo H. Boudreau
Assistant Examiner—Andrew W. Johns
Attorney, Agent, or Firm—Lahive & Cockfield

[57] ABSTRACT

An apparatus and method for determining motility and other characteristics of cells in a fluid medium employing both the scattering and transmission of light through that medium and the absorption of shorter wavelength light by the cell with subsequent emission of fluorescent light. Both forms of light are imaged on an image detection apparatus, the output of which is analyzed as a function of time to produce the information concerning the characteristics of the cell.

18 Claims, 4 Drawing Sheets

FLUORESCENCE AND MOTILITY CHARACTERIZATION SYSTEM FOR CELLS, BACTERIA, AND PARTICLES IN FLUIDS

BACKGROUND OF THE INVENTION

This invention relates to characterization of particles suspended in a fluidic medium. In particular, the invention is directed to an apparatus and method for simultaneously characterizing the fluorescence and motility of cell, bacteria and particles in fluids.

Conventional cell characterization systems generally employ characterization techniques that are directed to either conventional fluorescence measurements or conventional motility measurements using primarily visible light. Cell characterization systems utilizing visible light to interrogate the specimen provide standard motility parameters and cell count. Systems employing a fluorescence technique provide standard fluorescent parameters such as membrane integrity.

The motion of unstained cells is utilized to identify motion characteristics of living cells in standard microscopy. In the context of semen analysis identifying the motion characteristics includes determining for example the sperm motility and mean sperm velocity where sperm motility is understood as that fraction of sperm moving among the sperm in the specimen sample. Cell characterization, and primarily sperm motility characterization, is regularly utilized for animals, such as horses and bulls, to establish the reproductive quality of their sperm which is integral in the evaluation of their breeding potential. In addition, motility analysis is important in the diagnosis of reproductive abnormalities in human males.

Conventional techniques of cell characterization to measure standard motility parameters primarily utilize illumination in the visible light spectrum. A radiation generating source, emitting radiation in the visible light spectrum, is directed onto a specimen and the light is refracted by both the fluidic medium and the cells contained therein. The refracted light is conditioned and directed, by appropriate optics, onto a light sensitive device which measures light incident thereon. Utilizing conventional electronics and data processing techniques, the refracted light is analyzed for desired information, for example, standard cell motility parameters.

Examination of fluorescing cells is utilized in microbiology to provide information on cell membrane integrity and, with respect to sperm cells, acrosomal integrity. The acrosome, a baglike structure surrounding the head of the sperm cell, must be substantially intact and able to withstand acrosomal reaction for spermatozoa to penetrate the zona pellucida surrounding the ovum. The characterization of the acrosome integrity is of great importance in reproduction study and abnormality diagnosis. In addition to acrosomal integrity, characterizing fluorescing cells provides detailed cell fluorescence and motility information, for example, cell brightness and cell velocity.

Generally, fluorescence is induced by the illumination of a specimen stained with an appropriate fluorophore wherein the wavelength of the illumination is substantially within the fluorophore absorption peak bandwidth. The fluorophore absorbs the shorter wavelength radiation and, due to the fluorescing characteristics of the fluorophore, causes photon emission at a wavelength longer than that of the irradiating illumination. In addition, the emitted photons tend to have a wavelength within the visible light wavelength spectrum. The wavelength of the emitted photons is substantially dependent upon the fluorescence characteristics of the fluorophore and the wavelength of the irradiating illumination.

Fluorescent light characterization systems frequently employ ultra violet light to stimulate cells which are stained with a fluorophore dye. The ultra violet light generating source is directed onto a specimen stained with a fluorescence dye and, as described above, the specimen absorbs the ultra violet radiation. The dye, within both the cells and fluidic medium comprising the specimen, emits photons having wavelengths in the visible light spectrum. As in the case of refracted light, the emitted light is conditioned and directed, by appropriate optics, onto a light sensitive device which measures light incident thereon. Generally, the radiation sensitive device is an eyepiece or a camera in an instrument which often is a microscope. Appropriate electronics and data processing techniques are again used to obtain desired information.

A primary shortcoming of the conventional fluorescent light characterization systems is the techniques employed to induce fluorescence. The excitation radiation is generally a continuously irradiating source. The intense irradiation of the specimen is phototoxic and consequently destroys the living cells under investigation. In addition, these systems employ excitation radiation having wavelength characteristics that are also substantially phototoxic and, as described above, generally results in destruction of the living cell. As a result of the phototoxic effects, systems employing such techniques generally fail to accurately characterize general cell motility parameters as well as membrane integrity and cell fluorescent intensity.

In addition, conventional fluorescent light characterization system do not employ techniques to permit rapid assessment of the quantitative estimates of fluorescent brightness directly. This feature would permit a determination of the quantity of fluorophore present in the cell on an absolute scale. Conventional systems utilize a technique providing relative estimates of the amount of fluorophore present and thus fail to accurately characterize a crucial property of the cell.

SUMMARY OF THE INVENTION

Broadly speaking, the present invention provides a system for simultaneously characterizing the motility and fluorescence of specimen including cells, bacteria and particles in a fluidic medium. The system includes an illumination source for generating a first illuminating beam and directing it onto the specimen where it will be absorbed by said cell, bacteria or particle. The wavelength of this source is selected such that the cells, bacteria or particles will absorb it and emit fluorescent light at a second, longer wavelength.

The system further includes a second illumination source for generating a second illuminating beam at a wavelength which is longer than the first illuminating beam. The second illumination beam is directed onto the specimen where it will be transmitted through the specimen.

An imaging element is positioned to receive light transmitted through the specimen, light scattered by the specimen, and emitted from fluorescent light and direct it onto a radiation sensing element. A fluorescent filter element is positioned to intercept the emitted light directed by the imaging element and attenuate unwanted wavelengths of that light.

The system may further include an optical phase-shift element for translating the phase of predetermined portions of the transmitted light without substantially translating the phase of the scattered light. The optical phase shift element may include an optical phase-shift plate, positioned to intercept the transmitted light, having an optically retarding portion to provide a negative phase contrast image of the refracted light. Conversely, the optical phase-shift element may include an optical phase-shift plate positioned so as to optically retard the scattered light, to provide a positive phase contrast image of said refracted light.

The radiation sensing element generates output signals representative of the intensity of a light beam incident thereon. The radiation sensing element may includes an array of radiation detectors, wherein each detector generates an intensity signal representative of the intensity of the portion of a light beam incident thereon. Suitable radiation detectors include charge coupled devices or the like.

A microprocessor element, having a timing element and a processing element, provides timing signals to the illumination sources, and processes and generates the motility and fluorescence information. The timing element, coupled to the first illumination source and the second illumination source, generates control signals whereby the first and second illumination sources in response to the control signals generate the first and second illumination beams each for a short period and in an intercalated non-overlapping sequence. The processing element, coupled to the timing element and the radiation sensing element and further being responsive to the sensing element output signals, generates the cell motility parameters and the cell fluorescence information.

In another embodiment of the invention, the first illumination source generates an illumination beam at least one wavelength. The illumination beam is selectively filtered thereby providing an incident radiation beam having a wavelength selected from a plurality of predetermined wavelengths. A fluorescent filter element, having a plurality of pass bands, is correlated to the illumination sequence to attenuate unwanted wavelengths of the emitted light which correspond to the wavelength of the incident beam.

In yet another embodiment of the invention, at least two illumination sources generate, in an non-overlapping intercalated sequence, illumination beams where each is absorbed by said cell, bacteria or particle. As in the previous embodiment, a fluorescent filter element, having a plurality of pass bands, is correlated to the illumination sequence to attenuate unwanted wavelengths of the emitted light which correspond to the wavelength of the incident beam.

BRIEF DESCRIPTION OF THE DRAWINGS

The foregoing and other objects of this invention, the various features thereof, as well as the invention itself, may be more fully understood from the following description, when read together with the accompanying drawings in which.

DESCRIPTION OF THE PREFERRED EMBODIMENT

Figure 1:
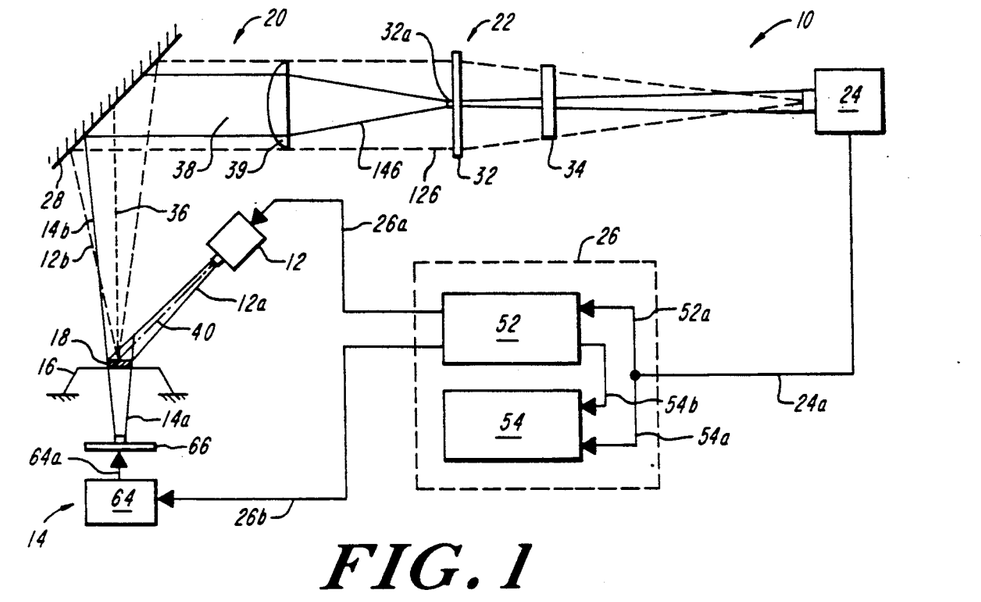
FIG. 1 illustrates in schematic form an exemplary embodiment of the cell motility and fluorescence characterization system in accordance with the present invention.

FIG. 1 shows a preferred embodiment of a cell motility and fluorescence characterization system in accordance with the present invention. The system may be considered as a combination of three subsystems. One such subsystem includes the light sources directing both fluorescence exciting and illuminating light onto a specimen; a second subsystem includes the optical system for directing the resultant light beams from the specimen onto a radiation detecting device. This system also provides for some modification of the resultant light beams. A third subsystem is a timing and analysis system which provides for intercalated operation of the light sources as well as analysis of data received from the detector.

The light source subsystem includes an illumination unit 14 having a visible or infra red light illumination source 66, powered by a switching power supply 64, for directing a beam 14a within the visible light spectrum onto a specimen 18 supported on specimen holder 16. This subsystem also includes fluorescence excitation unit 12 which generates radiation having a wavelength capable of exciting fluorescence in the specimen and directs the output beam 12a along axis 40 to impinge upon specimen 18.

The second subsystem directs both transmitted and scattered light and fluorescently emitted light from the specimen 18 along an optical path onto the radiation sensing unit 24. In the illustration of FIG. 1, the optical beams from the specimen are redirected by reflector 28 through imaging lens 30, optical phase shift assembly 32 and fluorescent filter assembly 34 onto radiation sensing unit 24.

The third subsystem generally is comprised of microprocessing unit 26 which includes a timing unit 52 and a data processing unit 54. The timing 52 provides output timing control signals to both light source 12 and power supply 64 of light source 14. The timing unit 52 is also interconnected to the radiation sensing unit 24. Signals indicative of the timing sequence of signals provided to the light sources as well as signals provided to or from radiation sensing unit 24 are provided to data processing unit 54. In addition, electrical signals resulting from the detection of incident light at radiation sensing unit 24 are provided as an input to data processing unit 54.

As earlier indicated, the primary function of the overall system is to provide for illumination of the cells to be tested with both illuminating light in the visible region, which light will be refracted, depending upon the cell size, distribution and density and transmitted to form a first image at radiation sensing unit 24, and also to provide fluorescence exciting radiation onto the cell to be absorbed by appropriate fluorophore stains and re-emitted to produce a second image at radiation sensing unit 24. The timing circuit generates signals for appropriate intercalation of triggering the two different light sources so that interspersed images from the visible illumination and the emitted light are detected. The sequence of signals generated by the radiation sensing unit 24 in response to the light impingement upon it is delivered to data processing unit 54 to synchronize the processing and develop output information indicative of the fluorescence and motion parameters of the cells in the tested specimen.

FIG. 1 shows an exemplary embodiment of a cell motility and fluorescence characterization system 10 in accordance with the present invention. System 10 includes a fluorescence excitation unit 12, an illumination unit 14, a specimen holder 16 captively supporting specimen 18, an optic directing element 20, an optical conditioning element 22, a radiation sensing unit 24, for example, a camera or a charge couple device, and a microprocessing unit 26 including a timing unit 52 and a data processing unit 54.

In the illustrative embodiment, optic directing element 20 is comprised of reflector 28 and imaging lens 39. Reflector 28 is positioned to direct beams 12b and 14b propagating along axis 36, to propagate along axis 38 toward optical conditioning element 22 and radiation sensing unit 24. Imaging lens 39 is positioned transverse to propagation axis 38 defining an image plane that is parallel to the substantially planar surface of specimen holder 16 wherein specimen 18 lies.

Optical conditioning element 22 is comprised of an optical phase-shift element 32 and a fluorescent filter element 34. Optical phase-shift element 32 is positioned transverse to propagation axis 38. In addition, fluorescent filter element 34 is also positioned transverse to propagation axis 38.

Illumination unit 14 is comprised of a power supply 64 and a visible light illumination source 66, for example, a light emitting diode. The power supply is capable of providing appropriate electrical pulses to the light emitting diode. Illumination source 66 generates a radiation beam 14a having a wavelength substantially within the visible light spectrum, for example 660 nm, or 6600 angstroms. Illumination source 66 is positioned such that beam 14a is directed onto specimen 18 wherein the light scattered by specimen 18, beam 14b, propagates along axis 36.

In the illustrative embodiment, fluorescence excitation unit 12 is electrically connected, via line 26a, to timing unit 52. Illumination unit 14 is L electrically connected, via line 26b, to timing unit 52. Radiation sensing unit 24 is electrically connected to timing unit 52 and data processing unit 54 via lines 52a and 54a respectively. Data processing unit 54 is electrically connected, via line 54b, to time unit 52. In addition pulse power supply 66 is electrically connected, via line 64a, to illumination source 66.

Figure 2:
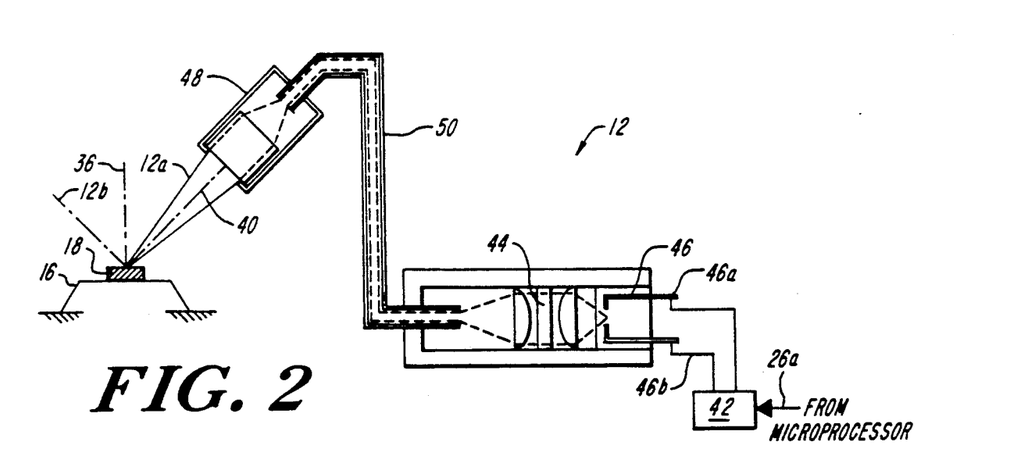
FIG. 2 illustrates in schematic form the fluorescent excitation unit of the characterization system of FIG. 1.

FIG. 2 illustrates a fluorescence excitation unit 12 in conjunction with specimen holder 16 and specimen 18 of system 10 of FIG. 1. Fluorescence excitation unit 12 is comprised of a trigger unit 42, a fluorescence excitation filter element 44, a radiation element 46, and an optical fiber element 50. Radiation element 46 generates radiation having a wavelength substantially within the ultra violet or visible spectrum, for example 350 to 690 nm, or 3500 to 6900 angstroms. Radiation element 46 is positioned such that the generated illumination is incident upon fluorescence excitation filter element 44. The filtered illumination is directed onto optical fiber element 50.

Optical fiber element 50 optically couples the filtered illumination of radiation element 46 to fluorescence directing element 48. Fluorescence directing element 48 is positioned such that beam 12a propagates along axis 40 and is incident upon specimen 18, and beam 12b, the fluorescent light emitted by the fluorophore contained within specimen 18, propagates substantially along axis 36 toward reflector 28.

In operation, timing unit 52 commands, in an non-overlapping intercalated sequence, fluorescence excitation unit 12 and illumination unit 14 to generate an associated illumination beam. The resultant transmitted/scattered or fluorescently emitted beam, 14b or 12b respectively, is directed by reflector 28 to propagate along propagation axis 38. Optical conditioning unit 22 conditions the beams such that the transmitted beam is translate into primarily an amplitude modulated wave and the emitted beam is filtered to isolate and pass radiation having a wavelength substantially within the visible light spectrum and thereby attenuate radiation having a wavelength consistent with beam 14a. The modified refracted and emitted beams are focused on the aperture of radiation sensing unit 24 which generates analog signals in response to the incident radiation. Microprocessor unit 26, and in particular data processing unit 54, receives the analog signals, generates a digital representation and processes the data for desired information.

In particular, radiation sensing unit 24 transmits an acquisition ready signal to timing unit 52. Timing unit 52 in response generates a trigger signal to either fluorescent excitation unit 12 or illumination unit 14. Any desired non-overlapping intercalated illumination sequence may be employed. Timing unit 52 is synchronized to data processing unit 54 which employs various processing techniques depending upon which excitation unit was utilized in generating the data. For the purpose of clarity and brevity and without intending to limit the invention to any specific illumination sequence, timing unit 52 in response to a first acquisition ready signal, generates a first trigger signal which is applied to standard fluorescent excitation unit 14, and in response to a second acquisition ready signal, generates a second trigger signal which is applied to fluorescent excitation unit 12.

In response to the first trigger signal, applied on line 26b, pulsed power supply 64 delivers sufficient electrical power to visible or infrared light illumination source 66 to generate radiation beam 14a. Beam 14a has a wavelength within the visible light spectrum and has temporal characteristics consistent with the trigger signal. The pulse width of illumination beam 14a is typically 3 to 6 milliseconds wherein the trigger signal frequency is typically 60 Hz.

Beam 14a is incident upon specimen 18 and is partially transmitted and partially scattered by the cells and fluidic medium within specimen 18. Transmitted beam 14b propagates along propagation axis 36 and is redirected by reflector element 28 to propagate along propagation axis 38. Beam 14b is incident upon imaging lens 39 which is spatially positioned and optically designed to form beam 14b onto retarding disk 32a of optical phase shift element 32.

Generally, unstained cells are virtually transparent and thereby provide little contrast with the fluidic medium of specimen 18. Beam 14b results from beam 14a passing through the substantially transparent particles which retards the phase of the region of the wave occupied by the cells. Thus the emerging wave is no longer perfectly planar but contains a phase modulated portion resulting from the delay of the wave caused by the cells in specimen 18. Optical phase shift element 32 is utilized to create a phase contrast image, either positive or negative. Optical phase shift element 32 substantially translates beam 14b, which is primarily a phase modulated wave, into a primarily amplitude modulated wave having either positive or negative phase contrast image property.

An amplitude modulated wave having a negative phase contrast image property is obtained by employing an optical phase shift element with a retarding disk. A negative phase contrast image property is such that the cells appear bright on a dark background. In contrast, an amplitude modulated wave having a positive phase contrast image property is obtained by employing an optical phase shift element with a retarding window. A positive phase contrast image property is such that the cells appear dark on a bright background.

Refracted beam 14b is then incident upon fluorescent filter element 34. Refracted beam 14b propagates through fluorescent filter element 34 without substantial attenuation. Fluorescent filter element 34 is designed to substantially attenuated radiation having a wavelength consistent with beam 12b, generated in fluorescence excitation unit 12 by short wavelength radiation element 46. Thus, the wavelength of refracted beam 14b is sufficiently long to pass through filter element 34, without substantial attenuation, onto the aperture of radiation sensing unit 24.

Radiation sensing unit 24 generates analog voltages representative of the intensity of the radiation beam incident upon its aperture. Data processing unit 54 acquires the analog voltages, generates a corresponding digital representation, and stores the digital data.

When radiation sensing unit 24 is prepared to acquire and measure the intensity of another image, sensing unit 24 transmits a data acquisition ready signal to timing unit 52 which generates the second trigger signal. For the reasons as described above, time unit 52 applies the second trigger signal, on line 26a, to fluorescence excitation unit 12. With reference to FIG. 2, and by way of example, in response to the second trigger signal trigger unit 42 generates a sufficient voltage differential across terminal 46a and 46b of radiation element 46 to cause ionization of the gas within element 46 resulting in photon emission having a broad band spectrum. The pulse width of the photon emission is typically 1 to 10 microseconds. Element 46 may consist of a laser, providing light at wavelengths suitable for fluorescent excitation.

The broad band radiation is directed onto fluorescence excitation filter element 44 which substantially attenuates photons having wavelengths that are outside the fluorophore absorption bandwidth. The pass band of filter element 44 is tailored to the fluorescence characteristics of the fluorophore used to stain specimen 18. The filtered radiation is directed onto optical fiber 50 which transmits the radiation to fluorescence directing unit 48. Fluorescence directing unit 48 focuses filtered radiation beam 12a onto specimen 18 to induce fluorescence of the fluorophore within specimen 18. Fluorescence directing unit 48 may be spatially positioned such that the angle of incidence of beam 12a is close to the normal, thereby reducing any backscattering effects.

As described above, beam 12a is substantially absorbed by the fluorophore which re-radiates, generally within 100 nanoseconds. Emitted radiation beam 12b has a wavelength within the visible light spectrum while the particular characteristics are dependent upon the wavelength of beam 12a and the fluorescence characteristics of the fluorophore used in staining specimen 18. With reference to FIG. 1, the emitted fluorescent light beam 12b, propagates along axis 36 and is redirected by reflector 28 to propagate along axis 38. Emitted beam 12b is incident upon imaging lens 39 which is further spatially positioned and designed to focus beam 12b on the aperture of radiation sensing unit 24 without substantial energy loss in propagating through optical phase shift element 32. Beam 12b avoids substantial energy loss by avoiding the central attenuating phase-shift region, retarding disk 32a, of optical phase shift element 32.

Emitted beam 12b is then incident upon fluorescent filter element 34. As described above, fluorescent filter element 34 is designed to substantially attenuate radiation having a wavelength consistent with beam 12b, generated by short wavelength radiation element 46. The wavelength of emitted beam 12b is sufficiently long to propagate through filter element 34 without substantial attenuation; however, energy having a wavelength consistent with beam 12a is substantially attenuated. The pass band characteristics of fluorescent filter element 34, as with fluorescence excitation filter element 44, are tailored to the fluorescence characteristics of the fluorophore used to stain specimen 18.

The modified emitted beam 12b is then incident upon the aperture of radiation sensing unit 24. As described previously, radiation sensing unit 24 generates analog voltages representative of the intensity of the radiation beam incident upon its aperture. Data processing unit 54 acquires the analog voltages, generates a corresponding digital representation, and processes the acquired data.

Figure 3:
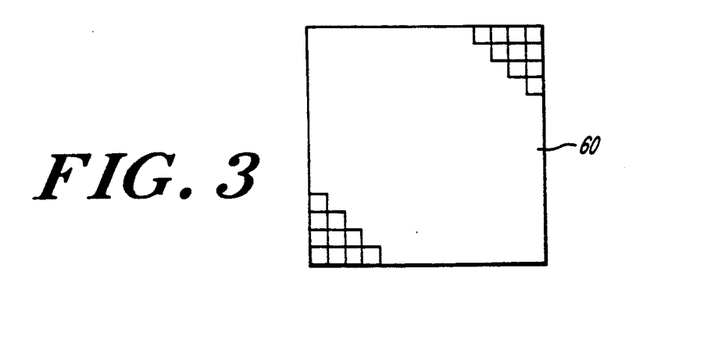
FIG. 3 depicts a internal configuration of the radiation sensing unit of FIG. 1.

Radiation sensing unit 24 may be, for example, a charge coupled device (CCD). FIG. 3 illustrates the sensing portion of radiation sensing unit 24 employing a CCD. Unit 24 includes an array of radiation sensing elements, defined as pixels. Each pixel generates an analog voltage signal representative of the illumination intensity of the radiation at the spatial location of the pixel. Such commercial manufactures as Honeywell, Philips, NEC and Xybion provide cameras specifying CCD pixel arrays typically to approximately $600 \times 500$. The pixel sensitivity is approximately $10^{-6}$ lux which is sufficient to measure the cell fluorescence intensities on the order of approximately $4 \times 10^{-4}$ lux for fluorescein based fluorophores present in cells at 1 ppm concentration. The radiation sensing unit may also included an image intensifier unit to increase the amount of light incident upon each pixel. Note, utilizing higher concentrations of fluorophore provides greater fluorescent illumination and consequently greater image contrast and definition.

As detailed above, data processing unit 54 acquires the analog data from radiation sensing unit 24. Processing unit 54 converts the analog data into digital data and stores the digital data as a frame in a memory array. Processing unit 54 analyzes each frame to identify the position of each cell. Data processing unit 54 further stores the frame sequence information as well as information pertaining to the excitation unit activated to generate the frame data. Comparison of frames generated by the same radiation source provides cell temporal variations. Furthermore, fluorescent frames provide information such as membrane integrity, acrosomal status, fluorescent intensity, and fluorescent cell tracks. It should be noted, data processing unit 54 may employ an identical analysis technique for data acquired from both visible light illumination and fluorescence illumination. In both cases, the specimen appears as bright cells against a dark background.

It should be noted that the fluorophore used may be for example, among others, fluorescein isothiocyanate, tetrarhodime isothiocyanate, 1-anilino-8-napthalene sulfonate, Hoechst 33258, Hoechst 33258, rodamine 123 and acridine orange. These stains characteristically bind primarily to the cell, or particular areas of interest within the cell, and generally not to the fluidic medium. Consequently, when the specimen is irradiated with the short wavelength radiation beam, the large amount of dye retained within the cell fluoresces strongly whereas the minimal amount of dye retained within the fluidic medium fluoresces weakly. Thus, the cells appear bright against a black background.

For example, 1-anilino-8-napthalene sulfonate (ANS) is a dye having the characteristics of emitting strong fluorescence when bound to for example hydrophobic regions of proteins in cells. However, in an aqueous solution, ANS is weakly fluorescent having an emission peak at 515 nm. Comparatively, the quantum yield of bound ANS is approximately 200 times greater than ANS in an aqueous solution while the emission peak shifts to 454 nm with an absorption peak at 350 nm. System 10 utilizes these characteristics to provide clear images of areas of interest within the cells wherein these areas appear bright against a dark background.

Figure 4:
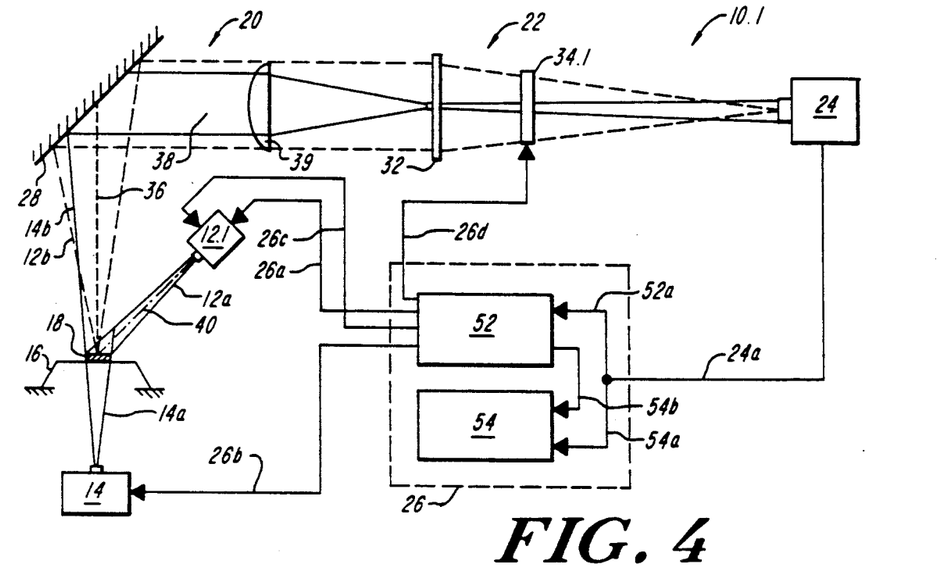
FIG. 4 illustrates in schematic form a second embodiment of the cell motility and fluorescence characterization system in accordance with the present invention.

A second embodiment of the present invention, illustrated in FIG. 4, offers the advantage of multiple fluorescence wavelength investigation. System 10.1 includes multiple wavelength fluorescence excitation units 12.1 and a multiple fluorescent filter element 34.1 wherein both are electrically connected to timing unit 52 via lines 26c and 26d respectively.

The operation of system 10.1 is substantially similar to system 10 of FIG. 1. System 10.1, however, utilizes multiple fluorescence excitation units 12.1 to provide a plurality of fluorescence excitation wavelengths to interrogate specimen 18. In addition, multiple fluorescent filter element 34.1 provides a plurality of pass bands to accommodate the plurality of fluorescence excitation wavelengths. Timing unit 52 synchronizes the multiple fluorescence wavelength interrogation in providing a pass band at fluorescent filter element 34.1 corresponding to the fluorescent light emitted by specimen 18. As described above, the characteristics of the fluorescent light emitted is dependent upon the excitation radiation generated by excitation unit 12.1 in inducing fluorescence. Thus, to insure proper operation timing unit 52 synchronizes the fluorescence excitation radiation and the band pass of the fluorescent filter. In addition, data processing unit 54 stores information pertaining to the interrogation wavelength with the frame data.

Figure 5:
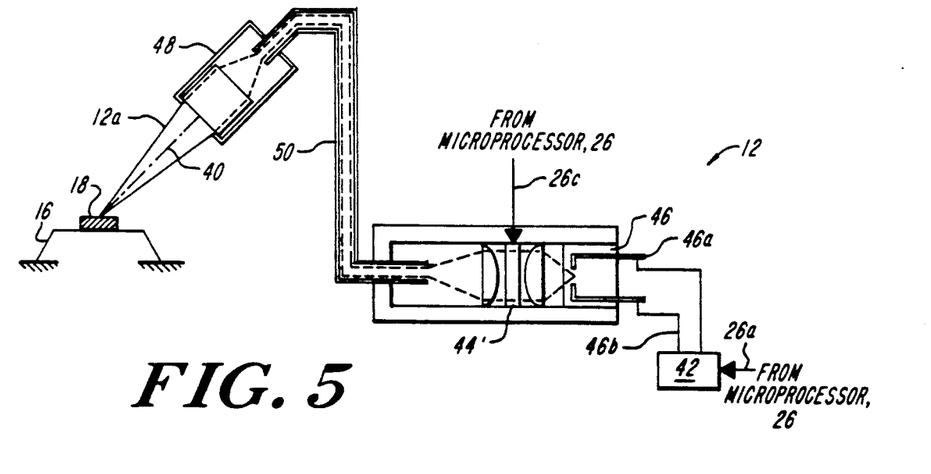
FIG. 5 illustrates in schematic form the fluorescent excitation unit of the system of FIG. 4.
Figure 6:
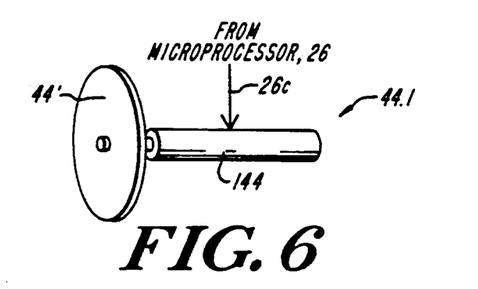
FIG. 6 illustrates in schematic form the fluorescent multiple wavelength excitation filter assembly of FIG. 5.

FIG. 5 illustrates multiple wavelength fluorescence excitation unit 12.1 of system 10.1 of FIG. 4. Fluorescence excitation unit 12.1 is substantially similar to unit 12 of FIG. 1, however, unit 12.1 includes a multiple fluorescence excitation filter element 44.1. FIG. 6 illustrates a multiple fluorescence excitation filter element 44.1 having a rotating disk type configuration. Fluorescent excitation filter element 44.1 includes a excitation filter disk element 44' which is mechanically coupled to motor element 144. Filter disk 44' is designed such that portions of the disk have predefined filtering characteristics. Motor element 144 rotates filter disk element 44' to alter that portion of the disk upon which the broad band radiation is incident and thereby redefine the wavelength of beam 12a. Motor element 144 is controlled, via line 26c, by timing unit 52 which synchronizes the pass band of excitation filter disk 44' with fluorescent filter element 34.1.

Figure 7:
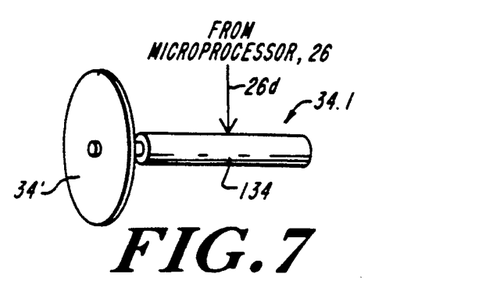
FIG. 7 illustrates in schematic form the fluorescent multiple wavelength filter assembly of FIG. 5.

FIG. 7 illustrates a multiple fluorescent filter element 34.1 having a rotating disk type configuration. Fluorescent excitation filter element 34.1 includes a excitation filter disk element 34' which is mechanically coupled to motor element 134. As with excitation filter element 44.1, fluorescent filter element 34.1 is designed such that portions of the disk provide predefined filtering characteristics substantially symmetrical to the filtering characteristics of excitation filter element 44.1. Motor element 134 rotates filter disk element 34' to alter that portion of the disk upon which the beam 12b is incident. Motor element 134 is controlled, via line 26d, by timing unit 52 which synchronizes the pass band of fluorescent filter disk element 34.1 with excitation filter element 44.1.

Figure 8:
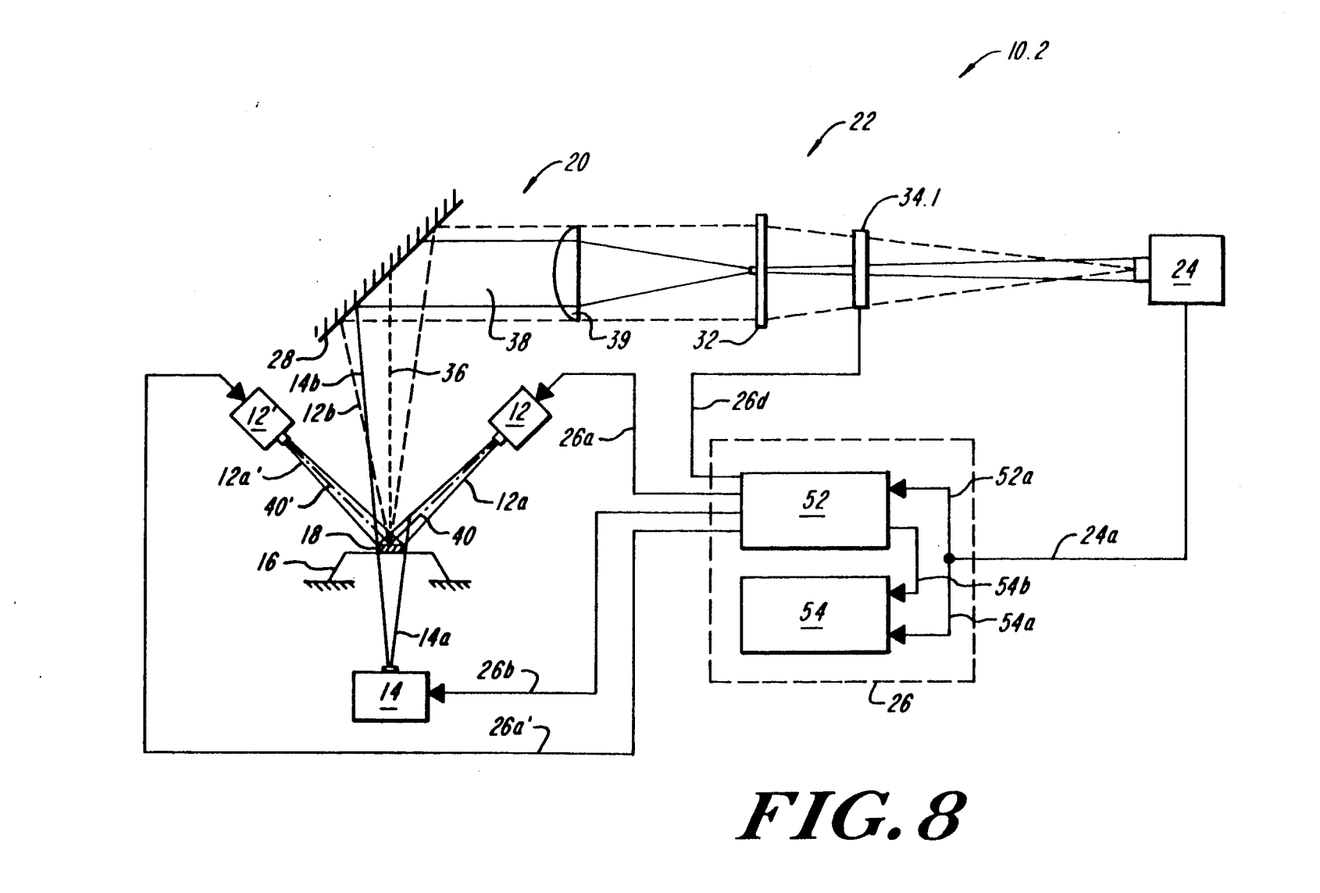
FIG. 8 illustrates in schematic form a third embodiment of the cell motility and fluorescence characterization system in accordance with the present invention.

FIG. 8 illustrates a third embodiment of the present invention which also offers the advantage of multiple fluorescence wavelength interrogation. System 10.2 includes multiple wavelength fluorescence excitation units 12 and a multiple fluorescent filter element 34.1 which is identical to filter element 34.1 of the second embodiment illustrated in FIG. 4. Each excitation unit 12 generates a short wavelength radiation beam 12b having an associated excitation wavelength. As described above, filter element 34.1 provides a plurality of pass bands to accommodate the plurality fluorescence excitation wavelengths. Timing unit 52 synchronizes excitation units 12 with filter element 24.1 to insure a proper pass band within the propagation path of beam 12b.

As with all the previous embodiments, the excitation units are triggered in an intercalated fashion. Consequently, any triggering sequence may be employed wherein the triggering sequence may or may not be periodic. The data processing is synchronized with the triggering sequence to provide proper data analysis.

Figure 9:
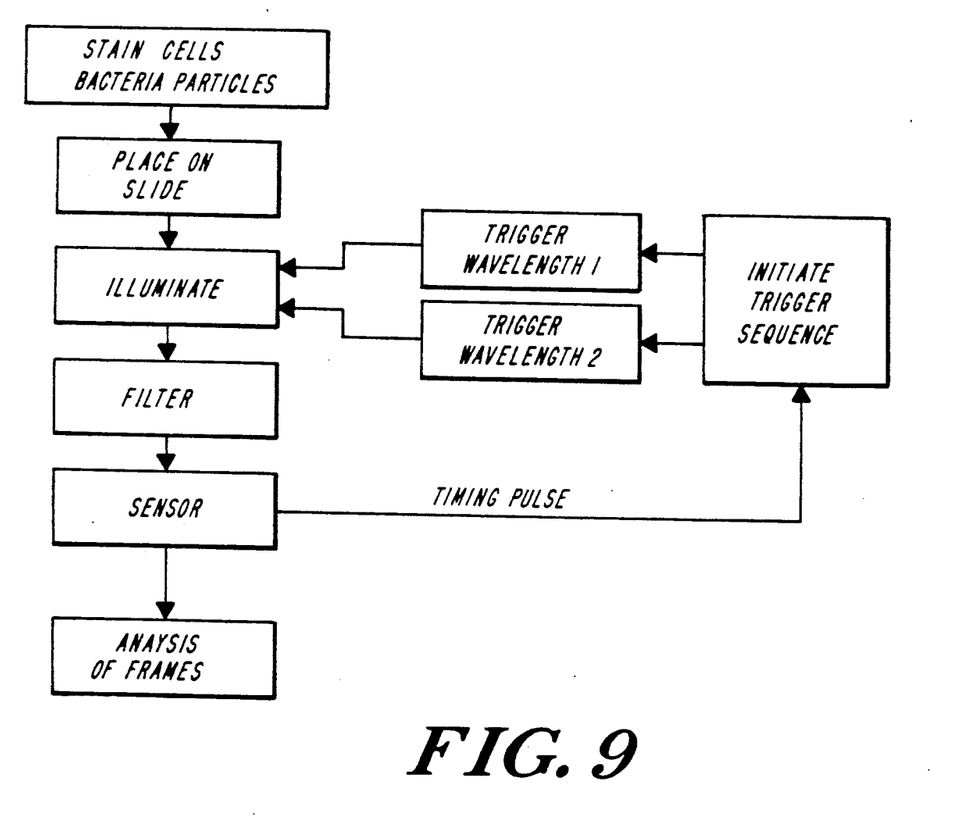
FIG. 9 is a flow chart illustrating a method of measuring characteristics and motility of cells, bacteria and particles in accordance with the principles of this invention.

FIG. 9 is a flow chart showing the steps of the method of this invention. The initial step is one of staining the cells, bacteria or particles, whose characteristics are to be measured, with a fluorescent dye and placing the stained cells, bacteria or particles on a support element such as a slide. A trigger sequence is initiated which first illuminates the specimen with light at a first wavelength that is absorbed by the dye and reemits light at a longer wavelength, then illuminates the specimen with light at a second wavelength, longer than the first, and transmits light refracted from the second illumination and light emitted from the dye through a filter, which attenuates all wavelengths shorter than this first wavelength. This filtered light is transmitted onto a sensor which provides output signals in response to received radiation. These output signals are analyzed to determine the characteristics of the specimens. The triggering sequences are arranged so that short periods of light at the first wavelength are intercalated with periods of light at the second wavelength. The sensor generates a timing signal to control the trigger sequence.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. An imaging system for characterizing fluorescence and motility of cells, bacteria or particles in a fluidic medium contained within a specimen comprising:
    a first illumination source for generating a first illuminating beam at a first wavelength such that when absorbed by one of said cells, bacteria or particles, said cells, bacteria or particles will emit fluorescent light at a second wavelength longer than said first wavelength,
    first means for directing said first illuminating beam onto said specimen;
    a second illumination source for generating a second illuminating beam at a third wavelength longer than said first wavelength such that it will be refracted and transmitted by said cell, bacteria or particle,
    second means for directing said second illuminating beam onto said specimen;
    a radiation sensing means for generating output signals representative of the intensity of a light beam incident thereon;
    an imaging means, positioned to receive light refracted by said specimen and light emitted from said specimen, for directing said refracted and emitted light as an imaging beam onto said radiation sensing means;
    a fluorescence filter formed such that it blocks substantially all radiation at a wavelength equal to or shorter than said first wavelength from reaching said radiation sensing means;
    a microprocessor unit including:
        timing means, coupled to said first illumination source and said second illumination source, for generating control signals whereby said first and second illumination sources in response to said control signals generate said first and second illumination beams each for a short period, and in an intercalated non-overlapping sequence; and
        processing means, coupled to said timing means and said radiation sensing means and further being responsive to said sensing means output signals, for generating motility and fluorescence information.

2. An imaging system in accordance with claim 1 wherein said system further includes an optical phase-shift means, positioned to intercept said transmitted and scattered light from said imaging means, for translating the phase of predetermined frequency portions of said refracted light without substantially translating the phase of said emitted light.

3. An imaging system in accordance with claim 2 wherein said optical phase shift means includes an optical phase-shift plate having an optically retarding portion intercepting said transmitted light to provide a negative phase contrast image of said cells, bacteria or particles.

4. An imaging system in accordance with claim 2 wherein said optical phase-shift means includes an optical phase-shift plate having an optically retarding portion intercepting said scattered light to provide a positive phase contrast image of said calls, bacteria or particles.

5. An imaging system in accordance with claim 1 wherein said radiation sensing means includes an array of radiation detectors, wherein each detector generates an intensity signal representative of the intensity of the portion of a light beam incident thereon.

6. An imaging system in accordance with claim 5 wherein said radiation detectors are charge coupled devices or the like.

7. An imaging system in accordance with claim 5 wherein said radiation detectors include an optical intensifier.

8. An imaging system in accordance with claim 1 wherein said imaging means includes an imaging lens positioned to establish an image plane wherein said specimen is spatially positioned within said image plane.

9. An imaging system in accordance with claim 1 wherein said radiation sensing means includes means for generating a timing signal whereby said timing means in response to said timing signal generates said control signals.

10. An imaging system in accordance with claim 1 wherein said fluorescence filter substantially attenuates said first wavelength without substantially attenuating said second and third wavelengths.

11. A method for measuring the characteristics and motility of cells, bacteria, and particles in a fluidic medium contained within a specimen comprising the steps of:
    staining the cells, bacteria, or particles with a fluorescent dye;
    irradiating said specimen with light at a first wavelength that it is absorbed by the fluorescent dye and emits light at a longer wavelength in response thereto;
    irradiating said specimen with light at a second wavelength substantially longer than the wavelength of light of said first irradiation;
    transmitting light of said second wavelength refracted by said specimen, and light emitted by said fluorescent dye in response to said first irradiation, through a filter, which attenuates substantially all radiation at a wavelength shorter than said first wavelength, onto a sensor which provides output signals in response to received radiation;
    triggering each of said first and second irradiation steps to provide said radiation for short periods, in which periods of irradiating at said first wavelength are intercalated with periods of irradiating at said second wavelength in non-overlapping relationship; and
    analyzing the output signals from the said sensor to determine the motility and other characteristics of said cells, bacteria, or particles.

12. A method in accordance with claim 11 further including transmitting light of said second wavelength, refracted by said specimen, through an optical phase delay plate which translates the phase of a predetermined frequency portions of said transmitted light without substantially translating the phase of said scattered light.

13. A method in accordance with claim 11 further including providing a negative phase contrast image of said refracted light.

14. A method in accordance with claim 11 further including providing a positive phase contrast image of said refracted light.

15. A method in accordance with claim 11 further including using an array of sensors to provide intensity signals representative of the intensity of the received light incident thereon.

16. A method in accordance with claim 15 wherein said array of sensors are charge coupled devices.

17. A method of claim 16 further including establishing an imaging plane wherein said specimen is spatially positioned.

18. A method in accordance with claim 16 further including providing signals indicative of said triggering to correlate said output signals with said first radiation step and second radiation step.

* * * * *

UNITED STATES PATENT AND TRADEMARK OFFICE
CERTIFICATE OF CORRECTION

PATENT NO. : 5,093,866
DATED : March 3, 1992
INVENTOR(S) : Douglas-Hamilton et al.

It is certified that error appears in the above-identified patent and that said Letters Patent is hereby corrected as shown below:

Column 3, line 40, after "beam" insert another --at--.

Column 5, line 58, delete "L".

Column 5, line 63, after "addition" insert --,--.

Column 6, line 27, delete "translate" and insert --translated--.

Signed and Sealed this

Fourth Day of January, 1994

Attest:

BRUCE LEHMAN

*Attesting Officer*  *Commissioner of Patents and Trademarks*